The following information is from the cover page of U.S. Patent 4,117,332.

United States Patent [19]

Felton et al.

[11] 4,117,332
[45] Sep. 26, 1978

[54] CIRCUIT FOR LINEARIZING THE RESPONSE OF AN ELECTRON CAPTURE DETECTOR

[75] Inventors: John Robert Felton, Antioch; Russell S. Gutow, Jr., Foster City, both of Calif.

[73] Assignee: Varian Associates, Inc., Palo Alto, Calif.

[21] Appl. No.: 661,467

[22] Filed: Feb. 26, 1976

[51] Int. Cl.$^2$ .............................................. G01T 1/18
[52] U.S. Cl. ................................... 250/374; 250/379; 250/386
[58] Field of Search ............... 250/374, 375, 379, 386, 250/388

[56] References Cited

U.S. PATENT DOCUMENTS

| Re. 28,951 | 8/1976 | Marshall et al. ................ 250/386 X |
| 3,897,344 | 7/1975 | Marshall et al. ................ 250/388 X |

Primary Examiner—Archie R. Borchelt
Attorney, Agent, or Firm—Stanley Z. Cole; Gerald M. Fisher; John J. Morrissey

[57] ABSTRACT

A circuit improvement is disclosed for use in an electron capture detector of the type including an electron capture cell, means for applying polarization pulses to the cell to derive a cell current, means for varying the pulse rate to maintain the cell current constant, and means for converting the pulse frequency to an analog signal indicative of the concentration of an electron-capturing component. Pursuant to the improvement, the pulse rate is varied by means which include an electrometer-amplifier for receiving the cell current and providing an output indicative of cell current departure from a reference current; an integrator for receiving the electrometer-amplifier output, the integrator generating a saw-tooth wave form, the slope of which is proportional to the magnitude of the electrometer-amplifier output signal; means for comparing the integrator output signal with a fixed reference voltage and for generating a triggering pulse when the two are equal; and pulse generator means coupled to the comparator output for generating the polarization pulses in response to the triggering pulses.

8 Claims, 1 Drawing Figure

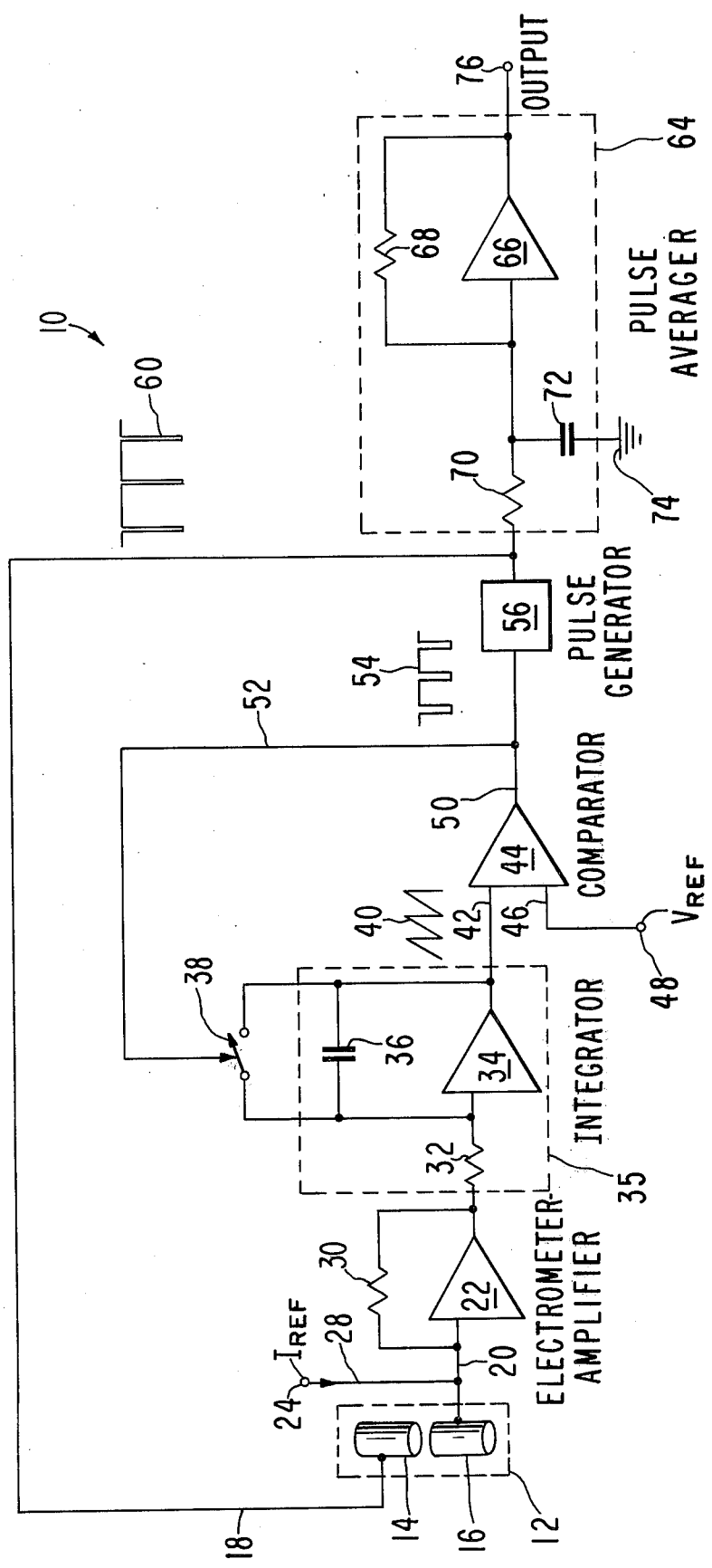

CIRCUIT FOR LINEARIZING THE RESPONSE OF AN ELECTRON CAPTURE DETECTOR

BACKGROUND OF INVENTION

This invention relates generally to gas analysis apparatus and methodology, and more specifically relates to an improved circuit for linearizing the response of an electron capture detector of the type utilized in gas chromatography systems or the like.

Within recent years, electron capture detectors have come into use in certain gas analysis environments. Such detectors are particularly applicable to gas chromatography systems — where their sensitivity enables detection of very low levels of electron-capturing components.

An electron capture detector includes a pair of spaced electrodes and a source of ionizing radiation as, for example, a short range beta source such as tritium contained in a quantity of titanium tritide. An electric field is established across the electrodes to produce a current of electrons migrating from an irradiated zone between the electrodes. In the absence of a gaseous compound which can capture the electrons, (e.g., in the case where only the pure carrier gas from a chromatographic column is being provided to the cell), a given cell current is produced. When an electron-capturing substance enters the cell, however, along with the carrier gas, some of the electrons are captured — with a resultant reduction in the number of free electrons and a consequent decline in the cell current. The resultant change in the current is thus an indication of the presence of the electron-capturing substance sought to be detected. By means of suitable circuitry changes in the cell current may be converted to values indicative of changes in the concentration of the electron-capturing substance.

In relatively early versions of the aforementioned electron capture detectors (ECD), DC techniques were utilized to apply a fixed potential difference between the electrodes of the detector in order to enable the aforementioned cell current. It was found, however, that such DC techniques tended to yield an unacceptably non-linear response. It was therefore proposed by a number of investigators to utilize instead a pulse sampling technique, pursuant to which the electrodes are polarized by a succession of short pulses. The pulse sampling technique was found to indeed improve the linearity characteristics of the detectors. Thus, for example, Lovelock, et al., in U.S. Pat. No. 3,634,754, disclosed a method for linearizing the response of an ECD intended primarily for use in gas chromatography applications. According to such method, a pulsed voltage is supplied at variable frequency to an ECD, the detector current is sensed, and the voltage pulse frequency is varied to maintain the detector current constant. The resultant pulse frequency is then taken as an indication of the concentration of electron-absorbing compounds within the detector cell.

Improvements in the methodology of Lovelock are set forth in Marshall, et al., U.S. Pat. No. 3,671,740. In the Marshall, et al. circuitry, an electrometer-amplifier is coupled to the detector to provide a first output signal representative of the relative concentration of electron-capturing compounds within the cell. A ramp generator, including a resettable oscillator which exhibits a linear change of voltage with time, provides a second output signal of continuously varying magnitude. A signal comparator, which is coupled to the electrometer-amplifier and to the ramp generator, provides an output pulse when the output signals of the electrometer-amplifier and the ramp generator are equal. A pulse generator coupled to the comparator generates a train of pulses in response to triggering by the comparator output. Successive such pulses reset the the ramp generator, and clear the electron-capture detector cell of free electrons. A frequency-to-voltage converting means coupled to the pulse generator ouput provides an output voltage signal proportional to the frequency of the pulse train.

A key aspect of the Marshall, et al. circuitry is the means for comparing the output from the ramp generator with the output from the electrometer-amplifier. The output of this ramp generator consists of voltage V, which is an inverse saw-tooth wave created by the discharge of a capacitor C. In operation, the capacitor is initially charged to the potential $V_r$ of a fixed reference voltage. The capacitor is then connected to a current source I so that the capacitor discharges at a constant rate. The output of the ramp generator at any time $t$ is $V = V_r - It/C$ When V falls to a value equal to the output voltage of the electrometer-amplifier, the comparator causes the pulse generator to operate and the ramp capacitor is recharged to the potential $V_r$.

The fixed values I and C in the Marshall, et al. circuitry fix a maximum time required for the capacitor voltage V to decay completely to zero. This maximum decay time in turn establishes the lowest allowed frequency $f_o$ of operation of the pulse generator. Electronically, it is not possible with this arrangement for the pulse generator to operate at frequencies below $f_o$. This is a significant disadvantage where the circuitry is connected to an electron capture detector operating in conjunction with a gas chromatograph. The reason for this is that it is quite common for elevated temperatures within a gas chromatograph to cause "bleed" of contaminant gases into the carrier gas. Furthermore, it is common for the magnitude of this contaminant bleed change with time as the gas chromatograph is used to analyze samples. The bleed rate may thus increase or decrease. In either case, the electron capture detector and frequency modulated pulsed circuitry will commonly respond with a varying output signal baseline corresponding to either increasing or decreasing pulse frequency.

Where circuitry of the type set forth in Marshall, et al. is utilized, it is common practice in the prior art to manually adjust the current input to the electrometer-amplifier such that the pulse generator operates at or near its lowest frequency $f_o$ when carrier gas only is passing through the ECD, i.e., when there are no electronegative sample peaks. Because of varying bleed rates as mentioned above, it is not uncommon for the carrier gas environment within the ECD to change with time, sometimes in a direction such as to demand a pulse frequency even lower than $f_o$. However, the output signal of the circuitry is electronically prohibited from decreasing below a value corresponding to $f_o$, so that this output signal will no longer provide an accurate representation of the ionization environment actually existing within the ECD.

BRIEF SUMMARY OF INVENTION

Now in accordance with the present invention, an improved circuit is disclosed which overcomes the aforementioned deficiencies of the prior art circuitry.

Pursuant to the invention, the cell output current is combined with an adjustable reference current, and the combined signal is provided to an electrometer-amplifier, so that the net current input to the electrometer-amplifier is a function of the difference between the two currents. The DC output from the electrometer-amplifier is provided to an integrator, which produces a linear change-of-voltage-with-time output signal in which the rate of voltage change with time depends on the magnitude of the electrometer-amplifier output. The output from the integrator is provided to a comparator, which compares the integrator output with a fixed reference voltage and produces an output signal when the integrator output signal becomes of the same magnitude as the reference voltage.

The comparator output signal thus constitutes a series of triggering pulses, which are coupled to a pulse generator and also reset the integrator. The train of pulses produced by the pulse generator is coupled to the electron capture cell and to a pulse averager. Acting at the cell, these pulses polarize same to produce the cell current. The pulse averager, which is basically a frequency-to-voltage converter, produces an output signal proportional to the pulse frequency provided by the pulse generator. The pulse averager output may be observed and recorded by conventional means.

The elements of the present circuit function is such a manner that the frequency of the pulses is varied to maintain the average cell current equal to the reference current. Introduction of electron-absorbing samples into the cell causes the pulse frequency to increase so as to hold the cell current constant, with the change in frequency being measurable as a change in voltage output of the pulse averager. The frequency of the pulses in the present circuit is not restricted by any low frequency limit $f_o$. Rather, the pulse frequency is free to vary from pulses effectively completely off (i.e., a frequency of zero) to a condition wherein the pulses are completely on (i.e., a frequency of 1/1 pulse width). Hence, by means of the invention, drifting electron capture detector signals can be continually monitored, regardless of whether they drift in the direction of increasing or decreasing pulse frequency.

BRIEF DESCRIPTION OF DRAWING

The invention is diagrammatically illustrated, by way of example, in the drawing appended hereto in which:

The FIGURE is an electrical schematic diagram setting forth key elements of an ECD circuit in accordance with the principles of the invention.

DESCRIPTION OF PREFERRED EMBODIMENT

In the FIGURE appended hereto, a circuit 10 is set forth including the basic elements of the present invention. The circuit is shown in use with an electron capture cell schematically suggested at 12. Although the circuit is not limited to use with a specific type of EC cell, it may be assumed for present purposes that cell 12 is of a type such as that disclosed in U.S. Pat. No. 4,063,156 to by Paul L. Patterson entitled ASYMMETRIC CYLINDER ELECTRON CAPTURE DETECTOR, which is assigned to the assignee of the present invention. The detector cell disclosed in the Patterson patent is of the so-called asymmetric type and includes a pair of axially-spaced, generally cylindrical electrodes, which are suggested herein by the schematically shown cathode 14 and anode 16. In the Patterson patent, certain more specific geometrical relationships are disclosed with respect to the electrodes and their association with the remaining elements of the cell. These features are not set forth herein because they are not of the present invention, except as may be hereinbelow set forth; and neither is the relative scale of cathode 14 and anode 16 intended to be accurately depicted by the the present FIGURE. Similarly, various other features of the cell 12 are not set forth herein, such as the radiation source, the mode of gas introduction, and the direction of gas flow, because details of these elements are not essential to an understanding of the present invention.

It will, however, be noted that the nature of the electrode connections is such that both cathode 14 and anode 16 are electrically floating, i.e., both electrodes are insulated from ground and are mutually insulated from each other, except of course through the conduction path enabled through the cell. In the present arrangement, it will be further noted that the signal input to cathode 14 is via the connecting line 18. As will shortly be evident, it is contemplated in the preferred embodiment of the invention that negative-going pulses will be applied to cathode 14. These pulses effect repulsion of the electron charge in the vicinity of the cathode, with the electron thereupon being collected by anode 16, so that the electron current may then be provided via line 20 to an electrometer-amplifier 22, which is provided with a conventional feedback resistor 30.

A current source 24, which is preferably adjustable, provides a reference current $I_{ref}$ through a branch 28 to line 20, and thus to the electrometer-amplifier 22. The current thus provided to electrometer-amplifier 22 may be regarded as the difference between the reference current and the average cell current, i.e., the quantity $(I_{Ref} - I_c)$ where $I_c$ is the average cell current.

The output of electrometer-amplifier 22, which is at a DC level, is provided through a resistor 32 to an operational amplifier 34. Amplifier 34 together with resistor 32 and a capacitor 36 define an integrator 35; the values of capacitor 36 and resistor 32 determine the time constant for the integrator. A transistor switch 38 is connected in parallel with capacitor 36, so as to enable by its actuation the resetting of the integrator.

The output from integrator 35 is in the form 40 of a saw-tooth wave, the slope of the saw-tooth wave being a function of the magnitude of the electrometer-amplifier output signal provided to the integrator 35. This saw-tooth wave form 40 is thus provided in line 42, and serves as one input to a comparator 44. The other input to comparator 44, i.e., at line 46, is provided by a fixed reference voltage $V_{Ref}$ at 48. Comparator 44 so functions that a comparator output signal is provided at line 50 at the instant of time when the integrator signal in line 42 just equals the magnitude of the fixed reference voltage in line 46. The comparator output signal also is provided via a line 52 to enable the transistor switch 38, which then shorts capacitor 36 to reset integrator 35.

It will thus be seen that the output from comparator 44, i.e., in line 50, takes the wave form 54, which effectively constitutes a series of triggering pulses. These triggering pulses are provided to a pulse generator 56, the output of which constitutes a series of negative-going pulses, as is illustrated by the wave form 60. This output, i.e., the output from pulse generator 56, is provided on the one hand through the line 18 to cathode 14 of cell 12; and on the other hand, the pulsed output is provided to a pulse averager 64, consisting of operational amplifier 66, a feed back resistor 68, a resistor 70, and the capacitor 72 which is connected to ground at 74. Resistor 70 and capacitor 72 together function as an RC filter for the pulses proceeding to the pulse averager 64. The pulse averager effectively constitutes a frequency-to-voltage converter, as is known in the art; and the output 76 from the pulse averager may be provided to a recorder or visually displayed.

With the aid of the foregoing, the operation of the present circuit may now be readily appreciated. The basic operation is such that the frequency of the pulses proceeding from pulse generator 56 maintains the average cell current $I_c$ equal to the average reference current $I_{ref}$. Assuming, for example, that the circuit 10 is being utilized in the gas chromatography environment heretofore discussed, and that quantities of an electronegative gaseous material enter into the carrier gas introduced into cell 12, the cell current in line 20 will tend to be diminished (i.e., the quantity of available electrons is decreased, making the quantity $|-I|$ smaller) so that the input signal to electrometer-amplifier 22 shows an incipient rising characteristic. The electrometer-amplifier output in turn rises, and this increases the slope of the saw-tooth wave form 40. In turn this increases the trigger pulse rate from comparator 44, thus increasing the frequency of the negative-going pulses 60, generated by pulse generator 56. These pulses 60 acting in feedback relationship at cathode 14, will increase the electron current flow from cell 12, i.e., the number of electrons collected at anode 16 is restored, to rebalance the circuit loop and restore stability.

Conversely, and by a similar consideration of the action effected herein, it will be evident that as the concentration of the electronegative substances introduced into cell 12 decreases, the frequency rate of pulses 60 will drop accordingly. The frequency rate may theoretically approach zero — although in practice the parameters of the present circuit are preferably so selected that, even at very low concentrations (or in the effective absence) of electronegative materials, a minimal frequency rate will be provided in order to maintain a stable feedback operation through the loop.

While the present invention has been particularly set forth in terms of specific embodiments thereof, it will be understood in view of the instant disclosure that numerous variations upon the invention are now enabled to those skilled in the art, which variations yet reside within the scope of the present teaching. Accordingly, the invention is to be broadly construed, and is limited only by the scope and spirit of the claims now appended hereto.

We claim:

1. In combination with an electron capture detector of the type including an electron capture cell having a pair of spaced electrodes, means for introducing a gas to be analyzed into said cell; an improved circuit for applying polarizing pulses to said cell and deriving an output signal indicative of the concentration of an electron capturing component of said gas, said circuit comprising:
    an electrometer-amplifier;
    a source for providing a reference current;
    means for combining said reference current with the current output from said cell generated in response to said polarizing pulses, and for providing the combined current to said electrometer-amplifier to thereby provide an output signal from said electrometer-amplifier indicative of the difference between said reference and cell currents;
    an integrator connected to receive the output signal from said electrometer-amplifier, said integrator producing a linear change of voltage with time output signal, the rate of voltage change with time being proportional to the magnitude of said electrometer-amplifier output signal;
    a comparator connected to compare the output signal from said integrator with a fixed reference voltage for generating a triggering pulse output signal when said integrator output signal equals said fixed reference voltage;
    means connected to receive said comparator output signal for resetting said integrator upon the occurrence of a triggering pulse at said comparator;
    pulse generator means coupled to said comparator for generating pulses in response to triggering pulses from said comparator;
    means connecting said pulses from said pulse generator means in feedback relationship to said cell to provide a pulsed polarizing potential across said electrodes in accordance with the frequency of the pulses produced by said pulse generator means; and
    pulse averager means connected to the output of said pulse generator means for producing an output voltage signal proportional to said pulse frequency.

2. A circuit in accordance with claim 1 wherein said electrodes comprise a cathode and an anode mutually insulated from each other and from ground; and wherein the pulses from said pulse generator are negative-going pulses and are applied to said cathode.

3. A circuit in accordance with claim 1 wherein said means providing said reference current is adjustable to provide a desired reference current level.

4. A circuit in accordance with claim 2 wherein said cell is characterized by an asymmetrical electrode configuration.

5. In an electron capture detector of the type including an electron capture cell, means for applying polarization pulses to said cell to derive a cell current, means for varying the pulse rate to said cell to maintain the cell current constant, and means for converting the frequency of said pulses to an analog signal indicative of the concentration of an electron capturing component of a gas in said cell; the improvement wherein said means for varying said pulse comprises:
    electrometer-amplifier means for receiving said cell current and providing an output signal indicative of departure of the cell current magnitude from the magnitude of a reference current;
    integrator means connected to receive the output of said electrometer-amplifier means, said integrator means producing an output signal having a saw-tooth wave form, the slope of the saw-tooth wave form being proportional to the magnitude of said electrometer-amplifier output signal;
    comparator means for comparing the output signal from said integrator means with a fixed reference voltage and for generating a triggering pulse when said integrator output signal equals said reference voltage; and
    pulse generator means coupled to said comparator means for generating pulses in response to said triggering pulses.

6. Apparatus in accordance with claim 5 further including means for resetting said integrator means upon the occurrence of a triggering pulse at said comparator means.

7. Apparatus in accordance with claim 6 wherein said cell is asymmetric and includes a cathode and an anode mutually insulated from each other and from ground; and wherein the pulses from said pulse generator are negative-going pulses and are applied to said cathode.

8. Apparatus in accordance with claim 6 wherein said reference current is provided by adjustable means, whereby a desired reference current level may be utilized.

* * * * *

UNITED STATES PATENT AND TRADEMARK OFFICE
CERTIFICATE OF CORRECTION

PATENT NO. : 4,117,332
DATED : September 26, 1978
INVENTOR(S) : John R. Felton; Russel S. Gutow, Jr.

It is certified that error appears in the above-identified patent and that said Letters Patent are hereby corrected as shown below:

Column 3, line 39, change "1/1" to --$1/\lambda$--.

Signed and Sealed this

Nineteenth Day of May 1981

[SEAL]

Attest:

RENE D. TEGTMEYER

Attesting Officer     Acting Commissioner of Patents and Trademarks